United States Patent
Boulos et al.

(10) Patent No.: US 9,447,016 B2
(45) Date of Patent: Sep. 20, 2016

(54) METHOD FOR THE PREPARATION OF TRIGLYCERIDES OF MEDIUM-CHAIN LENGTH FATTY ACIDS

(71) Applicant: PROMETIC BIOSCIENCES INC., Laval (CA)

(72) Inventors: Zacharie Boulos, Laval (CA); Jean-Simon Duceppe, St. Jérôme (CA); Christopher Penney, Pierrefonds (CA)

(73) Assignee: Prometic Pharma SMT Limited, Comberton, Cambridge (GB)

( * ) Notice: Subject to any disclaimer, the term of this patent is extended or adjusted under 35 U.S.C. 154(b) by 83 days.

(21) Appl. No.: 14/382,080

(22) PCT Filed: Feb. 28, 2013

(86) PCT No.: PCT/CA2013/000174
§ 371 (c)(1),
(2) Date: Aug. 29, 2014

(87) PCT Pub. No.: WO2013/126990
PCT Pub. Date: Sep. 6, 2013

(65) Prior Publication Data
US 2015/0018295 A1    Jan. 15, 2015

Related U.S. Application Data

(60) Provisional application No. 61/605,489, filed on Mar. 1, 2012.

(51) Int. Cl.
| | |
|---|---|
| *A23D 9/00* | (2006.01) |
| *C07C 67/08* | (2006.01) |
| *A61K 47/14* | (2006.01) |
| *C11C 3/02* | (2006.01) |
| *A61K 31/225* | (2006.01) |
| *A61K 31/23* | (2006.01) |
| *A61K 31/337* | (2006.01) |
| *A61K 31/513* | (2006.01) |
| *A61K 31/675* | (2006.01) |
| *A61K 31/704* | (2006.01) |
| *A61K 31/7068* | (2006.01) |
| *A61K 45/06* | (2006.01) |

(52) U.S. Cl.
CPC .............. *C07C 67/08* (2013.01); *A61K 31/225* (2013.01); *A61K 31/23* (2013.01); *A61K 31/337* (2013.01); *A61K 31/513* (2013.01); *A61K 31/675* (2013.01); *A61K 31/704* (2013.01); *A61K 31/7068* (2013.01); *A61K 45/06* (2013.01); *A61K 47/14* (2013.01); *C11C 3/02* (2013.01); *C11C 3/025* (2013.01)

(58) Field of Classification Search
CPC ......... C07C 67/08; C11C 3/02; C11C 3/025; A61K 31/225; A61K 31/23; A61K 31/337
USPC ......................................................... 554/227
See application file for complete search history.

(56) References Cited

U.S. PATENT DOCUMENTS 7,745,488 B2 * 6/2010 Gagnon ................. A61K 31/18
514/517

FOREIGN PATENT DOCUMENTS

| CN | 1594274 A | 3/2005 | |
|---|---|---|---|
| EP | 1592416 A1 * | 11/2005 | ............. A61K 31/20 |
| EP | 1592416 B1 | 1/2009 | |
| GB | 978085 A | 12/1964 | |

OTHER PUBLICATIONS

International Search Report and Written Opinion for corresponding Application No. PCT/CA2013/000174 (mailed Jul. 11, 2013).

* cited by examiner

*Primary Examiner* — Deborah D Carr
(74) *Attorney, Agent, or Firm* — LeClairRyan, a Professional Corporation

(57) ABSTRACT

A method is disclosed for the preparation of glycerol esters (triglycerides) of medium-chain length monocarboxylic fatty acids which consists of the reaction of the precursor free fatty acid and glycerol in the presence of a catalyst under partial vacuum. The process preferably uses a metal catalyst such as an oxide or a chloride of tungsten, molybdenum, calcium, zinc, chromium or magnesium. The method of the invention allows the preparation in high yield and high purity (>99.5%) of the final triglyceride. The present method allows the formation of triglycerides without solvent. Are also contemplated, the triglyceride obtained by the method, and the pharmaceutical composition containing the triglyceride as an excipient or as an active ingredient.

33 Claims, No Drawings

METHOD FOR THE PREPARATION OF TRIGLYCERIDES OF MEDIUM-CHAIN LENGTH FATTY ACIDS

This application is a national stage application under 35 U.S.C. §371 of PCT Application No. PCT/CA2013/000174, filed Feb. 28, 2013, which claims the priority benefit of U.S. Provisional Patent Application No. 61/605,489, filed Mar. 1, 2012.

FIELD OF THE INVENTION

A method is disclosed for the preparation of glycerol esters (triglycerides) of medium-chain length monocarboxylic fatty acids which consists of the reaction of the precursor free fatty acid and glycerol in the presence of a catalyst under partial vacuum. The present method allows the formation of triglycerides without solvent. The process preferably uses a metal catalyst such as an oxide or a chloride of tungsten, molybdenum, calcium, zinc, chromium or magnesium. The method of the invention allows the preparation in high yield and high purity (>99.5%) of the final triglyceride. The present method is particularly convenient for large-scale preparation of triglycerides of medium-chain length fatty acids.

BACKGROUND OF THE INVENTION

Triglycerides of medium-chain length fatty acids, known as medium-chain triglyceride(s) or MCT(s), can be synthesized by esterifying glycerol with fatty acids of carbon chain lengths of C8 (octanoic acid or caprylic acid) or C10 (decanoic acid or capric acid). MCTs are usually commercially available as a mixture of glycerol esters of C8 and C10 fatty acids, with small amounts (≤1% of each) of glycerol esters of C6 (hexanoic acid or caproic acid) and C12 (dodecanoic acid or lauric acid).

MCTs and their constituent medium-chain fatty acids are nontoxic materials which are used in the food and pharmaceutical industries. For example, Traul K. A. et al. (Food and Chemical Toxicology 38:79-98, 2000) state that MCTs have been utilized in an increasing number of food and nutrition applications. Also, it was reported by Roach, R. R. (Cereal Chem. 73(2):197-98, 1996) that tricaprin (triglyceride of C10), usually in mixtures with tricaprylin (triglycerides of C8), is used as an antifoaming and antistatic agent for plastics, lubricants, water treatment, and release agents for bakery products and candies. In addition, MCTs are also used primarily as emulsifiers in various human and veterinary pharmaceutical preparations and in cosmetics. U.S. Pat. No. 7,745,488 describes the use of medium-chain fatty acids or metallic salts or triglycerides or MCTs as an inducer of hematopoiesis. There are a number of toxicology studies which support the safety of MCTs. For example, the safety of human dietary consumption of MCTs, up to 1 g/kg, has been confirmed in several clinical trials. In fact, according to part 170 of the Code of Federal Regulations (CFR), the U.S. Food and Drug Administration (FDA) has granted triglycerides of fatty acids as GRAS (Generally Recognized As Safe) status for use as a food ingredient. Also, a literature review regarding the use of triglycerides such as tricaprin or tricaprylin in cosmetics supported the safety of these compounds (International Journal of Toxicology 2001, (20), 61-94). Similarly, the Cosmetic Ingredient Review (CIR) Expert Panel concluded that tricaprin and tricaprylin are safe with regard to the present practices of use and concentration in cosmetics (Elder, R. L. et al. J. Environ. Pathol. Toxicol. 4: 105-120, 1980). U.S. Pat. No. 4,602,040 describes another application of MCTs as a pharmaceutical excipient. More recently, MCTs were used for formulating existing drugs for enhancement of palatability and stability (Pharmaceutical Development and Technology, 2003, Vol. 8, (1), 111-115) or for improvement of drug distribution/solubility profile. In fact, the use of triglycerides for formulation of poorly water-soluble drugs has been investigated by different approaches which include nanoparticles, micelles and emulsions. For example, the oral bioavailability of the slightly water-soluble drug anethole trithione was enhanced by use of an MCT sub-microemulsion formulation (Si-Fei, H et al., International Journal of Pharmaceutics 2009, 379 (1), 18-24). Also, the antitumor efficacy and absorption of the poorly water soluble cancer drug paclitaxel has been improved by the use of MCT as a vehicle (Hong, J. W. et al. Mol. Cancer Ther. 2007, 6(12) 3239-47; US patent application 2006/0104999).

As typically known in the art, the MCTs are obtained by the reaction of glycerol with medium-chain length fatty acids in the presence of an acid and at high temperature (140-260° C.) or with the use of an enzyme such as lipase at 70-90° C. The low purity of the triglyceride obtained by these known techniques necessitates decolourization and chromatographic purification/distillation which makes large-scale synthesis difficult. In general, the yield and the purity obtained by these known techniques does not exceed 75% due to incomplete esterification and the loss of the product during workup and purification.

There is a need for improving the yield of synthesis of MCTs. There is also a need for simplifying its process of preparation in view of large-scale preparation.

SUMMARY OF THE INVENTION

An aspect of the present invention concerns a method for the preparation of a triglyceride of medium-chain length fatty acids comprising the steps of:
a) mixing glycerol with a three molar equivalents or an excess of said medium-chain length fatty acids, wherein each of the medium-chain length fatty acids contains a chain of 6 to 12 carbons;
b) reacting the mixture of step (a) with a divalent or trivalent metal cation catalyst; and
c) heating at a temperature of 160° C. or more, under partial vacuum, for a period of time sufficient to form the triglyceride. Said temperature is preferably from about 160° C. to about 180° C., and preferably of about 170° C. to about 175° C., and more preferably of about 175° C. Said period of time is preferably between 8 to 24 h, and more preferably about 22 h.

Since the glycerol has three sites of reaction for attaching a medium-chain length fatty acid, a stoichiometric equivalent of medium-chain length fatty acids means three molar equivalents, or three molecules of medium-chain length fatty acids for one molecule of glycerol. An excess of medium-chain length fatty acids means more than three molecules of medium-chain length fatty acids for one molecule of glycerol, or more than three molar equivalents. In a preferred embodiment, glycerol is mixed with more than three equivalents of medium-chain length fatty acids. In another preferred embodiment, glycerol is mixed with at least four molar equivalents of medium-chain length fatty acids.

In a preferred embodiment, the partial vacuum is from about 1 mm Hg to about 20 mm Hg, and preferably about 5 mm Hg to about 15 mm Hg, and more preferably of about 10 mm Hg.

In a preferred embodiment, the metal salt catalyst is tungsten oxide, tungsten chloride, tungsten carbonyl, calcium oxide, calcium chloride, magnesium oxide, magnesium chloride, zinc oxide, zinc chloride, magnesium oxide, magnesium chloride, molybdenum oxide, molybdenum chloride, chromium oxide, or chromium chloride. Preferred catalysts include tungsten oxide, tungsten chloride, calcium oxide, calcium chloride, magnesium oxide, magnesium chloride, zinc oxide, zinc chloride, magnesium oxide, magnesium chloride, molybdenum oxide, molybdenum chloride, chromium oxide, and chromium chloride. A most preferred catalyst is calcium oxide. Another most preferred catalyst is tungsten oxide. A further most preferred catalyst is zinc oxide. The amount of catalyst is preferably from about 0.5% to about 2.5% (w/w), more preferably from about 1% to about 2% (w/w).

In a preferred embodiment, each of the medium-chain length fatty acids contains either a chain of 6 carbons, 8 carbons, 10 carbons or 12 carbons.

In a preferred embodiment, the medium-chain length fatty acids comprise a mixture of fatty acid having a chain of 8 carbons and fatty acid having a chain of 10 carbons.

In an embodiment where the medium-chain length fatty acids contain chains of 8 to 12 carbons, the method further comprises recovery steps, which comprise the steps of:
 d) removing the partial vacuum;
 e) cooling at a temperature of 80° C. or less;
 f) adding hot alcohol so as to form an alcoholic solution, where the hot alcohol has a temperature varying from about 60° C. to the alcohol boiling point temperature, preferably of about 80° C.;
 g) filtering the alcoholic solution and obtaining a filtrated solution; and
 h) maintaining the filtrated solution at a temperature between about 0° C. to about 20° C., preferably from about 0° C. to about 5° C., for a period of time sufficient for crystallizing the formed triglyceride, preferably for a period of at least 1 hour, and more preferably for a period of about 2 hours.

It is considered that removing partial vacuum means that the solution is brought back to normal or ambient atmospheric pressure.

In a preferred embodiment of the present invention, the hot alcohol is ethanol or isopropanol. In another preferred embodiment, the hot alcohol is ethanol and its temperature is of about 80° C. The volume of hot alcohol is preferably the volume that is necessary for dissolving the triglyceride being formed.

The step of filtering the alcoholic solution prior to cooling down and crystallization allows removal of solid impurities that could be present.

In a preferred embodiment, the process further comprises an additional step of adding cold alcohol to the filtrated solution before maintaining the cold temperature during which the crystallization occurs. The cold alcohol has preferably a temperature from about 0° C. to about 5° C., and more preferably of about 0° C. The addition of cold alcohol is contributes to cool down the triglyceride and to crystallize it.

In a preferred embodiment, the cold alcohol is the same type of alcohol than the hot alcohol. The volume of cold alcohol is preferably the volume that is useful for cooling down the triglyceride.

The medium-chain length fatty acids of 6 to 7 carbons are volatile fatty acids and therefore the recovery steps need to be adapted to this characteristic. In an embodiment where the medium-chain length fatty acids contain chains of 6 to 7 carbons, the method further comprises recovery steps, which comprises the steps of:
 d) removing the partial vacuum;
 e) cooling at a temperature of 80° C. or less;
 f) adding an organic solvent for dissolving the triglyceride so as to form an organic solution;
 g) adding an aqueous solution of sodium hydroxide to the organic solution; the aqueous solution being preferably 1-2% NaOH;
 h) recovering the organic solution and discarding the aqueous solution;
 i) treating the organic solution with a drying agent;
 j) filtrating the organic solution through silica gel;
 k) treating the organic solution with a drying agent; and
 l) evaporating the organic solvent.

In a preferred embodiment of the invention, the organic solvent is hexane, dichloromethane, ethyl acetate or ether. The volume of organic solvent is preferably the volume that is necessary to solubilize all triglycerides being formed by the reaction. The filtration over silica gel allows a rapid purification of the triglycerides. The silica gel is preferably in the form of a pad i.e. a silica gel pad. The washing step with the aqueous solution of sodium hydroxide allows removal of non-reacted fatty acids. The step of treating with a drying agent is a well known treatment in the chemistry field which comprises the step of adding a drying agent to the solution and removing the drying agent by filtration. The amount of drying agent is preferably the amount that is necessary to capture all the molecules of water left in the organic solution. In a preferred embodiment of the invention, the drying agent is magnesium sulfate or sodium sulfate.

In a preferred embodiment of the invention, the catalyst is calcium oxide, tungsten oxide or zinc oxide; and the yield of the produced triglyceride is of 75 to 95%.

In a preferred embodiment of the invention, the method produces triglyceride at a yield of 75% to 95% and at a purity of at least 99% or 99.5%, wherein said method comprises the steps of:
 a) mixing glycerol with at least 3 molar equivalents of said medium-chain length fatty acids, wherein each of the medium-chain length fatty acids contains a chain of 8 to 12 carbons;
 b) reacting the mixture of step (a) with calcium oxide, tungsten oxide or zinc oxide;
 c) heating at a temperature of about 175° C., under partial vacuum of about 10 mm Hg, for a period of about 22 hours such that the triglyceride is formed;
 d) removing the partial vacuum;
 e) cooling at a temperature of 80° C. or less;
 f) adding hot alcohol having a temperature of about 80° C. so as to form an alcoholic solution;
 g) filtering the alcoholic solution and obtaining a filtrated solution; and
 h) maintaining the filtrated solution at a temperature between about 0° C. to about 5° C., for a period of about 2 hours.

In a preferred embodiment of the invention, the method produces triglyceride at a yield of 75% to 95% and at a purity of at least 99% or 99.5%, wherein said method comprises the steps of:

a) mixing glycerol with at least 3 molar equivalents of said medium-chain length fatty acids, wherein each of the medium-chain length fatty acids contains a chain of 6 to 7 carbons;
b) reacting the mixture of step (a) with calcium oxide, tungsten oxide or zinc oxide;
c) heating at a temperature of about 175° C., under partial vacuum of about 10 mm Hg, for a period of about 22 hours such that the triglyceride is formed;
d) removing the partial vacuum;
e) cooling at a temperature of 80° C. or less;
f) adding an organic solvent for dissolving the triglyceride so as to form an organic solution;
g) adding an aqueous solution of 1-2% NaOH;
h) recovering the organic solution and discarding the aqueous solution;
i) treating the organic solution with a drying agent;
j) filtering the organic solution through silica gel;
k) treating the organic solution with a drying agent; and
l) evaporating the organic solvent.

The present invention also concerns a triglyceride of medium-chain length fatty acids that is prepared by the method of the present invention.

In a preferred embodiment of the invention, the triglyceride of medium-chain length fatty acids prepared by the method of the present invention has purity of at least 99%, and more preferably, the triglyceride has purity of at least 99.5%.

The present invention further concerns a pharmaceutical formulation which comprises the triglyceride of medium-chain length fatty acids of the present invention as an excipient. The triglyceride may be appreciated for different characteristics including its ability to improve the solubilization of active ingredient having poor water solubility. The concentration of triglyceride in the pharmaceutical formulation may vary between about 50% to about 90% (w/w), preferably between about 70% and about 80% (w/w), and most preferably about 80% (w/w).

In a preferred embodiment of the invention, the pharmaceutical formulation further comprises from about 25 to about 75% (w/w) of ethyl decanoate and from about 2.5 to about 10% (w/w) of ethanol.

In a preferred embodiment of the invention, the pharmaceutical formulation further comprises an active ingredient being solubilized therein. Advantageously, the active ingredient has a water solubility of less than about 1 mg/100 ml. Examples of active ingredients that can advantageously benefit from the formulation of the present invention, are paclitaxel, gemcitabine, cyclophosphamide, doxorubicin and 5-fluorouracil.

An aspect of the present invention concerns a pharmaceutical composition comprising the triglyceride of medium-chain length fatty acid(s) of the present invention as an active ingredient. In the pharmaceutical composition, the triglyceride is preferably in a therapeutically effective amount. The triglycerides of medium-chain length fatty acids are known to have many therapeutic effects and therefore, its therapeutic active amount may vary depending on the desired therapeutic effect. The concentration of triglyceride in the pharmaceutical composition may vary preferably between 50% and 100% (W/W).

In a thirteenth preferred embodiment of the invention, the pharmaceutical composition further comprises a second active ingredient. The second active ingredient may or may not benefit from a synergic effect from its combination with the triglyceride. Such second active ingredient can be paclitaxel, gemcitabine, cyclophosphamide, doxorubicin or 5-fluorouracil.

DESCRIPTION OF SPECIFIC EMBODIMENTS OF THE INVENTION

The present invention provides an improved process for the synthesis of triglyceride of medium-chain length fatty acids (i.e., a chain length of from six to twelve carbon atoms). Glycerol is reacted with excess free fatty acid, preferably of at least three molar equivalents, and more preferably four molar equivalents. The free fatty acid has a desired chain length that is advantageously selected from C6 to C12. According to the present invention, the reaction of the glycerol with the free fatty acid is performed in the presence of a catalyst and in absence of a solvent. The reaction is undertaken under partial vacuum and at a temperature varying between 160-180° C. (preferably 175° C.) to produce the triglyceride product. A partial vacuum as contemplated in the present invention is a low vacuum that can be achieved in a laboratory with rudimentary equipment where the pressure is lower than the atmospheric pressure and higher than 1 mm Hg or 1 Torr. The process advantageously allows synthesis of triglyceride without solvent. The combination of the catalyst, partial vacuum and heat offers ideal conditions for esterification of glycerol with medium-chain length fatty acids, such that all medium-chain length fatty acids react with a hydroxyl group of the glycerol. Thus, when an excess of medium-chain length fatty acids is present with the glycerol in the conditions of the present invention, all, or almost all, hydroxyl groups of the glycerol are esterified with a medium-chain length fatty acid.

The catalyst of the present invention is a metal salt catalyst. Such a metal salt may be an oxide or a chloride of one of the following metal: tungsten, calcium, magnesium, zinc, molybdenum or chromium. The preferred catalysts are the oxide of tungsten and the oxide of calcium. The preferred triglycerides prepared by the present method are the triglyceride of caprylic acid (C8 fatty acid), and the triglyceride of capric acid (C10 fatty acid).

Although compounds of the present invention are restricted to those products which are triesters of medium-chain length fatty acids with glycerol, it will be appreciated by those skilled in the art that certain structural modifications which lie outside of the claims of the invention, but which are nonetheless obvious, fall within the scope of the invention. For example, medium-chain length fatty acid diglycerides can be prepared by the present invention by replacing glycerol with serinol and so two molecules of medium-chain length fatty acids are esterified to the two hydroxyls of serinol, constitutes an obvious example. Similarly, medium-chain length fatty acid di- and monoglycerides wherein two molecules and one molecule respectively of medium-chain length fatty acid(s) are esterified to glycerol provides another obvious example. Additionally, it will be appreciated by those skilled in the art that we can use a source of medium-chain length fatty acids of various length of chain of carbons. As such, commercially available mixtures of medium-chain triglycerides (e.g., mixture of glycerol esters of C8 and C10 fatty acids in varying proportions) also constitute further obvious examples. Finally, in another aspect of this invention and in order to permit solubilization of otherwise insoluble drugs, medium-chain length triglycerides can be employed as delivery vehicle or excipient. Furthermore, ethyl decanoate and ethanol may be used as co-solvents.

Preferably, the triglyceride synthesized by the present process is recovered by crystallization and/or precipitation from cold alcohol. Such cold alcohol can be ethanol or isopropanol.

The problem currently exists to find a method that would afford a convenient large scale preparation of triglycerides of medium-chain length fatty acids in high yield, high purity and at a reasonable cost. It has been surprisingly found that when glycerol is mixed with a medium-chain fatty acid and heated under partial vacuum in the presence of metal oxide or chloride, the triglyceride product is obtained in high yield and purity after precipitation from ethanol. This high yield and purity overcomes the difficulties associated with large-scale purification by column chromatography/distillation. As shown in the following examples, purification is achieved by dissolving the crude product in alcohol which is subsequently cooled preferably in an ice bath to precipitate the pure triglyceride product.

Triglycerides of medium-chain length fatty acids refer to those triglycerides with monocarboxylic fatty acids having carbon chain lengths of 6 to 12 carbons including C6 (caproic acid, hexanoic acid), C8 (caprylic acid, octanoic acid), C10 (capric acid, decanoic acid) and C12 (lauric acid, dodecanoic acid). While even numbered carbon atom chain lengths constitute a preferred embodiment of this invention, odd numbered carbon atom chain length carboxylic acid triglycerides of glycerol may also be conveniently prepared in high product yield and purity. Odd numbered carbon atom chains include 7 (heptanoic acid), 9 (nonanoic acid) and 11 (undecanoic acid). According to preferred embodiments, triglycerides of a medium-chain fatty acids are tricaprate (tricaprin) and tricaprylate (tricaprylin). The reaction temperature is preferably 160° C. under partial vacuum of 10 mmHg and more preferably at 175° C. under the same vacuum. The latter condition completely removes by-product water formed during the reaction which accelerates formation of product triglycerides. Temperatures at less than 160° C. may be less desirable since this reduces the speed of the reaction and results in a reduced yield of the triglyceride product relative to free fatty acids and glycerol reactants. The crude product is preferably dissolved in cold ethanol, filtered and then crystallized from cold ethanol. Yields of 75% to 95% can be achieved by the appropriate selection of reactant ratios, temperature and length of reaction.

The triglycerides of the present invention may be formulated using pharmaceutically acceptable carriers by methods known to those skilled in the art (Merck Index, Merck & Co., Rahway, N.J.). These compositions include, but are not limited to, solids, liquids, oils, emulsions, gels, aerosols, inhalants, capsules, pills, patches and suppositories.

The triglycerides of the present invention also have different physical characteristics than ordinary fats, such as lower viscosities, solubility in alcohol, no greasy feel on the skin, and as such find special usefulness in the pharmaceutical and cosmetics and toiletries industries. However, due to its relatively high melting point, tricaprin and trilaurin can be used in solid compositions in contrast to the aforementioned mixed triglyceride or caprylic triglyceride.

The following examples are presented to illustrate the invention but not intended to limit the scope of the invention. These examples may be summarized by the equation below:

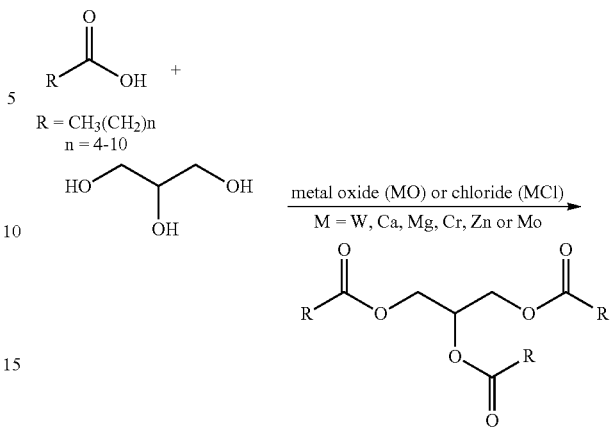

All HPLC chromatograms and mass spectra were recorded on an HP 1100 LC-MS Agilent instrument using an analytical Zorbax SB-phenyl column with a gradient over 8 minutes of 15-99% acetonitrile-water with 0.01% trifluoroacetic acid as the eluant and a flow of 2 mL/minute. An ELSD detector was used to analyze the triglycerides.

EXAMPLE 1

Tricaprin (Capric Acid: n=8)

To a 250-mL flask containing glycerol (5.0 g, 54.3 mmol) and equipped with a condenser, were added capric acid (37.4 g, 217.2 mmol) and calcium oxide (45.4 mg, 0.8 mmol). The mixture was heated at 175° C. under partial vacuum (1 Torr, water pump vacuum) for 22 hours. The temperature of the water in the condenser was approximately 35° C. in order to maintain a gentle reflux of the capric acid and to accelerate removal of water under vacuum. The reaction was cooled to room temperature and the residue dissolved in hot ethanol (95%, 400 mL). This solution was treated with charcoal, filtered over fiberglass and cooled in an ice bath at 0-5° C. for 2 hours. Tricaprin was crystallized as a white solid which was filtered and washed with cold ethanol (95%, 40 mL). Yield of product: 27.5 g (91%); mp 29-31° C.; $^1$H NMR (400 MHz, CDCl$_3$): δ 5.22-5.29 (m, 1H), 4.29 (dd, J=11.9, J=4.3, 2H), 4.14 (dd, J=11.9, J=6.1, 2H), 2.26-2.34 (m, 6H), 1.54-1.65 (m, 6H), 1.18-1.36 (m, 36H), 0.87 (t, J=7.0, 9H). $^{13}$C NMR (101 MHz, CDCl$_3$): δ 73.54, 173.13, 69.07, 62.32, 34.44, 34.27, 32.09, 29.67, 29.65, 29.51, 29.50, 29.34, 29.30, 25.13, 25.08, 22.90, 14.33; MS (ES) m/z 578 (M+Na$^+$); HPLC: 5.6 min.

EXAMPLE 2

Trilaurin (Lauric Acid: n=10)

Triglyceride of lauric acid was prepared as described in Example 1 by use of 15 g of lauric acid (74.9 mmol), 1.7 g glycerol (18.7 mmol) and 15.7 mg calcium oxide (0.28 mmol). Yield of product: 9 g (78%); mp=45-47° C.; $^1$H NMR (400 MHz, CDCl$_3$): δ 5.25-5.28 (m, 1H), 4.29 (dd, J=11.7, J=4.3, 2H), 4.14 (dd, J=11.9, J=6.1, 2H), 2.28-2.34 (m, 6H), 1.55-1.66 (m, 6H), 1.20-1.36 (m, 48H), 0.87 (t, J=7.0, 9H). $^{13}$C (101 MHz, CDCl$_3$): δ ?173.55, 173.14, 69.07, 62.33, 34.45, 34.29, 32.15, 29.86, 29.73, 29.71, 29.58, 29.53, 29.50, 29.35, 29.31, 25.10, 22.92, 14.36; HPLC: 6.5 min.

EXAMPLE 3

Tricaprylin (Caprylic Acid: n=6)

Triglyceride of caprylic acid was prepared as described in Example 1 by use of 11 g of caprylic acid (74.9 mmol), 1.7 g glycerol (18.7 mmol) and 15.7 mg calcium oxide (0.28 mmol). Since tricaprylin is a liquid, the crude product was filtered on silica gel, instead of fiberglass, using ethyl acetate/hexanes (5-10%). This gave the pure product as a colorless oil. Yield: 8 g (89%); $^1$H NMR (400 MHz, CDCl$_3$): δ 5.25-5.28 (m, 1H), 4.29 (dd, J=11.9, J=4.3, 2H), 4.14 (dd, J=11.9, J=6.1, 2H), 2.28-2.34 (m, 6H), 1.56-1.66 (m, 6H), 1.20-1.36 (m, 24H), 0.87 (t, J=7.0, 9H). $^{13}$C (101 MHz, CDCl$_3$): δ 173.56, 173.14, 69.07, 62.33, 34.45, 34.28, 31.89, 31.88, 29.28, 29.24, 29.16, 29.14, 25.13, 25.08, 22.83, 14.30; HPLC: 4.5 min.

EXAMPLE 4

Tricaproate (Caproic Acid: n=4)

Since tricaproate is a volatile compound, the procedure described in example 1 was slightly modified. The procedure detailed in Example 4 is applicable to the method of preparing the triglyceride with volatile medium-chain length fatty acids such as the fatty acids of chain of 6 to 7 carbons. In a 250 mL flask containing glycerol (1.73 g, 18.7 mmol), equipped with a condenser and a Dean-Stark trap filled with caproic acid, was added caproic acid (8.7 g, 74.9 mmol) and calcium oxide (15.7 mg, 0.3 mmol). The mixture was heated at 175° C. under vacuum overnight (22 hours, 10 mm Hg). The mixture was cooled and dissolved in ethyl acetate. This solution was washed with 10% sodium hydroxide, brine (NaCl), treated with magnesium sulfate-charcoal for water removal and filtered on fiberglass. The filtrate was concentrated to give a yellow oil which was dissolved in hexanes and poured on a 10×10 cm$^2$ silica gel pad. The compound was eluted with 10% ethyl acetate/hexanes. The pure fractions were combined and concentrated to give a colorless oil. Yield: 5.8 g, 80%; $^1$H NMR (400 MHz, CDCl$_3$): δ 5.23-5.29 (m, 1H), 4.29 (dd, J=11.9, J=4.3, 2H), 4.14 (dd, J=11.9, J=6.1, 2H), 2.27-2.34 (m, 6H), 1.56-1.66 (m, 6H), 1.22-1.37 (m, 12H), 0.89 (t, J=7.0, 9H). $^{13}$C (101 MHz, CDCl$_3$): δ 173.56, 173.14, 69.07, 62.32, 34.39, 34.23, 31.45, 31.41, 24.78, 24.75, 22.51, 14.12; HPLC: 3.8 min.

EXAMPLE 5

Yield of Triglycerides of Medium-Chain Length Fatty Acids Obtained with the Use of Different Metal Catalysts The synthesis of tricaproin, tricaprylin, tricaprin and trilaurin following the procedures described in examples 1-4 was undertaken except that the calcium oxide catalyst was replaced with magnesium, zinc, tungsten, molybdenum and chromium salts.

TABLE 1

Yield of triglycerides of medium-chain length fatty acids with the use of different catalysts.

| Triglyceride | Catalyst | Yield (%) |
| --- | --- | --- |
| $C_6$ | $WO_3$ | 85 |
|  | CaO | 80 |
| $C_8$ | $WO_3$ | 93 |
|  | CaO | 89 |
| $C_{10}$ | $WO_3$ | 93 |
|  | $W(CO)_6$ | 50.7 |
|  | $Na_2WO_4 \cdot 2H_2O$ | 90 |
|  | $WCl_6$ | 92 |
|  | $MoO_3$ | 74 |
|  | $MgCl_2$ | 76 |
|  | MgO | 82 |
|  | CaO | 91 |
|  | $CrO_3$ | 85 |
|  | $ZnCl_2$ | 89 |
|  | ZnO | 90 |
| $C_{12}$ | $WO_3$ | 77 |
|  | $MoO_3$ | 75 |
|  | CaO | 78 |

All modifications and substitutions that come within the meaning of the claims and the range of their legal equivalents are to be embraced within their scope.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method for the preparation of a triglyceride of medium-chain length fatty acids comprising the steps of:
    a) mixing glycerol with three molar equivalents or an excess of said medium-chain length fatty acids, wherein each of the medium-chain length fatty acids contains a chain of 6 to 12 carbons;
    b) reacting the mixture of step (a) with a divalent or trivalent metal cation catalyst; and
    c) heating at a temperature of 160° C. or more, under partial vacuum, for a period of time sufficient to form the triglyceride.

2. The method according to claim 1, wherein said glycerol is mixed with an excess of said fatty acids.

3. The method according to claim 1, wherein the temperature of heating at step (c) is about 175° C.

4. The method according to claim 1, wherein said partial vacuum is from about 1 to about 20 mm Hg.

5. The method according to claim 4, wherein said partial vacuum is about 10 mm Hg.

6. The method according to claim 4, wherein the heating step (c) is for a period of between 8 hours to 24 hours.

7. The method according to claim 1 wherein the catalyst is tungsten oxide, tungsten chloride, tungsten carbonyl, calcium oxide, calcium chloride, magnesium oxide, magnesium chloride, zinc oxide, zinc chloride, magnesium oxide, magnesium chloride, molybdenum oxide, molybdenum chloride, chromium oxide, or chromium chloride.

8. The method according to claim 7, wherein said catalyst is calcium oxide, tungsten oxide or zinc oxide.

9. The method according to claim 1, wherein each of the medium-chain length fatty acids contains a chain of 6 carbons.

10. The method according to claim 1, wherein each of the medium-chain length fatty acids contains a chain of 8 carbons.

11. The method according to claim 1, wherein each of the medium-chain length fatty acids contains a chain of 10 carbons.

12. The method according to claim 1, wherein each of the medium-chain length fatty acids contains a chain of 12 carbons.

13. The method according to claim 1, wherein the medium-chain length fatty acids comprise fatty acids having a chain of 8 carbons and fatty acids having a chain of 10 carbons.

14. The method according to claim 1, wherein each of the medium-chain length fatty acids contains a chain of 8 to 12 carbons, further comprising the step of:
 d) removing the partial vacuum;
 e) cooling at a temperature of 80° C. or less;
 f) adding hot alcohol so as to form an alcoholic solution, where the hot alcohol has a temperature varying from about 60° C. to the alcohol boiling point temperature;
 g) filtering the alcoholic solution and obtaining a filtrated solution; and
 h) maintaining the filtrated solution at a temperature between about 0° C. to about 20° C., for a period of time sufficient for crystallizing the formed triglyceride.

15. The method according to claim 14, wherein said hot alcohol is ethanol and has a temperature of about 80° C.

16. The method according to claim 14, further comprising the step of adding cold alcohol to the filtrated solution before step (h), wherein said cold alcohol has a temperature of about 0° C. to about 5° C.

17. The method according to claim 14, wherein the alcohol is ethanol or isopropanol.

18. The method according to claim 14, wherein the temperature is maintained at step (h) for at least 1 hour.

19. The method according to claim 1, wherein each of the medium-chain length fatty acids contains a chain of 6 to 7 carbons, further comprising the step of:
 d) removing the partial vacuum;
 e) cooling at a temperature of 80° C. or less;
 f) adding an organic solvent for dissolving the triglyceride so as to form an organic solution;
 g) adding an aqueous solution of sodium hydroxide to the organic solution;
 h) recovering the organic solution and discarding the aqueous solution;
 i) treating the organic solution with a drying agent;
 j) filtering the organic solution through silica gel;
 k) treating the organic solution with a drying agent; and
 l) evaporating the organic solvent.

20. The method according to claim 19, wherein the organic solvent is hexane, dichloromethane, ethyl acetate or ether.

21. The method according to claim 19, wherein the drying agent is magnesium sulfate or sodium sulfate.

22. The method according to claim 1, wherein the method produces triglyceride at a yield of 75% to 95% and at a purity of at least 99%, wherein
 step a) comprises mixing glycerol with at least 3 molar equivalents of said medium-chain length fatty acids, wherein each of the medium-chain length fatty acids contains a chain of 8 to 12 carbons;
 step b) comprises reacting the mixture of step (a) with calcium oxide, tungsten oxide or zinc oxide;
 step c) comprises heating at a temperature of about 175° C., under partial vacuum of about 10 mm Hg, for a period of about 22 hours such that the triglyceride is formed; and
wherein said method further comprises the steps of:
 d) removing the partial vacuum;
 e) cooling at a temperature of 80° C. or less;
 f) adding hot alcohol having a temperature of about 80° C. so as to form an alcoholic solution;
 g) filtering the alcoholic solution and obtaining a filtrated solution; and
 h) maintaining the filtrated solution at a temperature between about 0° C. to about 5° C., for a period of about 2 hours.

23. The method according to claim 1, wherein the method produces triglyceride at a yield of 75% to 95% and at a purity of at least 99%, wherein
 step a) comprises mixing glycerol with at least 3 molar equivalents of said medium-chain length fatty acids, wherein each of the medium-chain length fatty acids contains a chain of 6 to 7 carbons;
 step b) comprises reacting the mixture of step (a) with calcium oxide, tungsten oxide or zinc oxide;
 step c) comprises heating at a temperature of about 175° C., under partial vacuum of about 10 mm Hg, for a period of about 22 hours such that the triglyceride is formed; and
wherein said method further comprises the steps of:
 d) removing the partial vacuum;
 e) cooling at a temperature of 80° C. or less;
 f) adding an organic solvent for dissolving the triglyceride so as to form an organic solution;
 g) adding an aqueous solution of 1-2% (W/W) NaOH;
 h) recovering the organic solution and discarding the aqueous solution;
 i) treating the organic solution with a drying agent;
 j) filtering the organic solution through silica gel;
 k) treating the organic solution with a drying agent; and
 l) evaporating the organic solvent.

24. A pharmaceutical formulation comprising a triglyceride of medium-chain length fatty acids having a purity of at least 99%, wherein the medium-chain length fatty acid contains a chain of 6 to 12 carbons.

25. The pharmaceutical formulation of claim 24, wherein said triglyceride has a purity of at least 99.5%.

26. The pharmaceutical formulation of claim 24, wherein said triglyceride is an excipient.

27. The pharmaceutical formulation of claim 26, further comprising from about 25 to about 75% (w/w) of ethyl decanoate and from about 2.5 to about 10% (w/w) of ethanol.

28. The pharmaceutical formulation of claim 26, further comprising an active ingredient being solubilized therein.

29. The pharmaceutical formulation of claim 28, wherein said active ingredient has a water solubility of less than about 1 mg/100 ml.

30. The pharmaceutical formulation of claim 28, wherein the active ingredient is paclitaxel, gemcitabine, cyclophosphamide, doxorubicin or 5-fluorouracil.

31. The pharmaceutical formulation of claim 24, wherein said triglyceride is an active ingredient.

32. The pharmaceutical formulation of claim 31, further comprising a second active ingredient.

33. The pharmaceutical formulation of claim 32, wherein the second active ingredient is paclitaxel, gemcitabine, cyclophosphamide, doxorubicin or 5-fluorouracil.

* * * * *